Jan. 13, 1959 E. S. BOERNER Plant Pat. 1,798
CHRYSANTHEMUM PLANT
Filed June 3, 1958
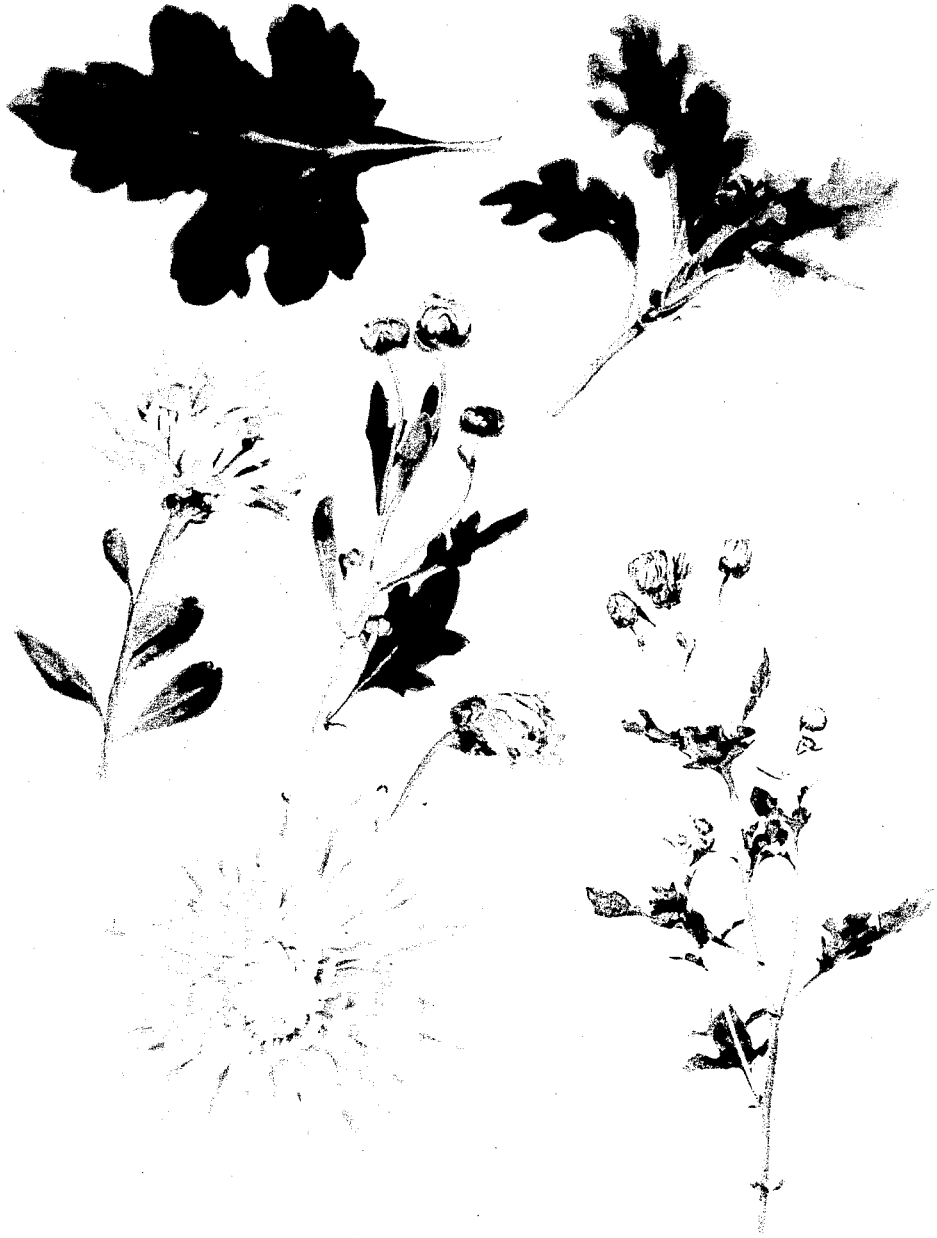
Inventor.
E. S. Boerner
By: Robb & Robb
Attorneys.

United States Patent Office

Plant Pat. 1,798
Patented Jan. 13, 1959

1,798

CHRYSANTHEMUM PLANT

Eugene S. Boerner, Newark, N. Y., assignor to Jackson & Perkins Company, Newark, N. Y., a corporation of New York Application June 3, 1958, Serial No. 739,641

1 Claim. (Cl. 47—60)

The present invention relates to a new and distinct variety of chrysanthemum plant of the decorative type, which was originated by me by crossing an unnamed and unpatented deep golden seedling of "Swallow" (Plant Patent No. 1,106) with the variety "Kingbird" (Plant Patent No. 1,306).

The primary objective of this breeding was to produce a new chrysanthemum variety in which the vigor and hardiness of the parent variety "Kingbird" is combined with the pastel color tones of the flower of the parent variety "Swallow." This objective was fully achieved, along with other improvements, as evidenced by the following characteristics which are outstanding in the new variety and which distinguish it from its parents as well as from all other varieties of which I am aware:

(1) A free and vigorous habit of growth;

(2) Free production of suckers, which is unusual for a chrysanthemum variety bearing flowers of this color;

(3) Good hardiness; and (4) A distinctive Light Coral Red general color tonality of the flowers.

Asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black-and-white, as illustrative of the form and habit of growth of the plant.

The following is a detailed description of the new variety, with color terminology in accordance with Ridgway's Color Standards and Nomenclature, as based upon observations made from specimens grown outdoors at Newark, New York, near mid-morning in the early part of October:

Parentage: An unnamed deep golden seedling of "Swallow" × "Kingbird."

Classification: Decorative, with center petals slightly incurved.

Growth: Vigorous; upright; very free; attains a height averaging about 30 inches.

Cold resistance: The plant is winter hardy in northern New York, and the flowers show little frost burn with early frosts.

Blooming period: In the Newark, New York climatic area, blooming begins in early October and continues until heavy frosts.

*Flower*

Bud:

*Color.*—When sepals first divide—Carrot Red, Plate 14. When petals begin to unfurl—Flesh Color, Plate 14. When half-blown: inside of petals—Light Jasper Red, Plate 13; outside of petals—Cream Color, Plate 16, lightly overcast with Jasper Pink, Plate 13.

*Peduncle.*—Strong. Color—Absinthe Green, Plate 31.

Bloom:

*Size.*—5 inches.

*Stem.*—Stiff.

*Form.*—Decorative, with center petals slightly incurved.

*Petalage.*—Double.

*Color.*—Center of flower—Pinard Yellow, Plate 4, lightly overcast with Light Jasper Red, Plate 13. Outer petals—Light Jasper Red, Plate 13, lightly overcast with Coral Pink, Plate 13. Base of petals—Clear Dull Green-Yellow, Plate 17. Inside of petals—Light Coral Red, Plate 13. Reverse of petals—Cartridge Buff, Plate 30, lightly overcast with Jasper Pink, Plate 13.

*Petals.*—Texture—stiff. Form—oval pointed.

*Fragrance.*—Characteristic chrysanthemum.

*Plant*

Form: Upright.

Growth: Bushy; vigorous; many suckers.

Foliage:

*Size.*—Large.

*Quantity.*—Normal.

*Color.*—Upper side—Varley's Green, Plate 18. Under side—Bice Green, Plate 17.

*Texture.*—Leathery.

I claim:

A new and distinct variety of chrysanthemum plant of the decorative type, substantially as herein shown and described, characterized particularly as to novelty by the unique combination of a free and vigorous habit of growth, an unusually free production of suckers, good winter hardiness, and a distinctive Light Coral Red general color tonality of the flowers.

No references cited.